(12) United States Patent
Baumann et al.

(10) Patent No.: US 7,820,110 B2
(45) Date of Patent: Oct. 26, 2010

(54) DROP CATCHER

(75) Inventors: Renato Baumann, Steinhausen (CH); Roland Bernet, Immensee (CH); Heinz Kerbler, Adligenswil (CH); Reto Schorno, Adligenswil (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 648 days.

(21) Appl. No.: 11/595,316

(22) Filed: Nov. 10, 2006

(65) Prior Publication Data

US 2007/0110626 A1 May 17, 2007

(30) Foreign Application Priority Data

Nov. 11, 2005 (EP) .................................. 05110647

(51) Int. Cl.
*B01L 3/00* (2006.01)
(52) U.S. Cl. .................... 422/100; 422/929; 73/1.74; 73/863.32; 73/864.24
(58) Field of Classification Search .................. 73/1.73, 73/1.74, 863.32, 863.33, 864.01–864.25; 422/100, 922–929
See application file for complete search history.

(56) References Cited

U.S. PATENT DOCUMENTS

| 4,347,520 | A | 8/1982 | Paranjpe et al. |
| 5,846,489 | A | 12/1998 | Bienhaus et al. |
| 6,921,513 | B2 | 7/2005 | Schubert et al. |
| 7,427,510 | B2 | 9/2008 | Schubert et al. |

| 2003/0075556 | A1 * | 4/2003 | Tajima et al. .................. 222/23 |

FOREIGN PATENT DOCUMENTS

| DE | 4314657 A1 | 11/1994 |
| EP | 1 110 609 B1 | 6/2001 |
| EP | 1508809 A1 | 2/2005 |
| EP | 1 701 275 A2 | 9/2006 |
| EP | 1508809 B1 | 2/2007 |
| WO | WO 97/46714 A2 | 12/1997 |
| WO | WO 03/097239 A1 | 11/2003 |

OTHER PUBLICATIONS

Hamilton Robotics, 2010, "FAME: Fully automated ELISA workstation", http://www.hamiltonrobotics.com/printlhamilton-robotics/liquidhandling/fame.*

(Continued)

*Primary Examiner*—Jill Warden
(74) *Attorney, Agent, or Firm*—Charles M. Doyle; Vivien Banholzer; Olga Kay

(57) ABSTRACT

The invention relates to a device for catching drops from a pipette mechanically attached to a pipetting device in the field of nucleic acid purification and amplification. Furthermore, a method for pipetting a liquid with a decreased potentiality of contamination of an analytical instrument as well as liquids or/and samples placed on said analytical instrument is provided. Moreover, an analytical instrument at least comprising a pipetting device, and a device for catching drops from a pipette mechanically attached to said pipetting device wherein the movement of the device for catching drops is coupled to the movement of said pipetting device is illustrated.

13 Claims, 7 Drawing Sheets

OTHER PUBLICATIONS

Hau, B., et al., 1993, "Mathematical Functions to Describe Disease Progress Curves of Double Sigmoid Pattern", *Ecology and Epidemiology*, 83:928-932.

Liu, W., et al., 2002, Validation of a quantitative method for Real time PCR kinetics, *Biochemical and Biophysical Research Communication*, 294: 347-352.

Zhao, S, et al., 2005, "Comprehensive Algorithm for Quantitative Real-Time Polymerase Reaction" *Journal of Computable Biology*, 12 (8):10471064.

* cited by examiner

DROP CATCHER

BACKGROUND OF THE INVENTION

This application claims the benefit of priority under 35 U.S.C. §119 of EP Application 05110647.4 filed Nov. 11, 2005, the contents of which are hereby incorporated by reference.

1. Field of the Invention

The present invention is directed to instruments, devices and methods for use in the fields of nucleic acid isolation and amplification.

2. Description of Related Art

Devices for catching drops for various applications are known in the art. WO200071330 describes a semi-automated lamination process and apparatus for laminating spherical and cylinder power ophthalmic lens blanks in a properly oriented alignment of the lens blanks. Herein, the apparatus may comprise a drip tray with a removable insert for catching a hardenable liquid adhesive from a syringe, which is located on the carriage underneath the syringe applicator at a distinct operating position. In particular, the drip tray is actively transported underneath the syringe for receiving the expended liquid adhesive, when the syringe is undergoing priming steps in order to reduce the occurrence of bubbles. Herein, the drip tray is not used to prevent the contamination of the apparatus by unintentional discharge of liquid, but as a reservoir for expended liquid during priming of the syringe. Furthermore, the movement of the drip tray is not mechanically coupled to the vertical movement of the syringe.

In the field of nucleic acid research and sample preparation drop catchers have been used in instruments such the MagNA Pure Compact or the MagNA PureLC (both manufactured by Roche Applied Science) to prevent unintentional discharge of liquid from the pipetting device. Both instruments contain oblong drop catchers, which are carried by the upper side of the magnet unit. Whenever the pipetting device is moved over the reagent/sample stage by a first actuator, the liquid drop catcher is actively placed underneath the pipetting device by a second actuator to prevent possible drops falling from the pipetting device onto the instrument and thereby contaminating the reagent/sample stage, reagents or other samples.

EP 1110609 discloses a multi-chamber assembly and a pipette assembly for processing fluid samples containing nucleic acids comprising a contamination guard for preventing fluid extracted from a first chamber dispersing into a second chamber. The pipette assembly has one movement action along the line of a row of sample chambers with an up and down movement action conducted by a first movement unit, while a second movement unit shifts the contamination guard in relation to the sample chambers. In one particular embodiment the contamination guard may also be attached to the pipette assembly. This embodiment has the disadvantage that the opening of the pipette assembly is not covered by the contamination guard when the pipette assembly is moved and therefore, may not receive and incorporate liquids escaping from the opening of the pipette assembly or dripping from the outer walls of the pipette assembly when the pipette assembly is withdrawn from the multi-chamber assembly.

EP 1508809 discloses a sample analyzer for nucleic acid detection comprising a droplet removing member. The movement of the droplet removing member is not mechanically coupled to the movement of the dispensing unit and therefore, necessitates the use of two separate actuators for driving these movements.

For integrated systems drop catchers as used in the MagNA Pure Compact, the MagNA PureLC instruments or as disclosed in EP 1110609 and EP 1508809 have the common disadvantage that an active movement of the drop catcher is performed by a second actuator independent of the movement of the pipetting device, which is conducted by a first actuator. However, the integration of a second actuator on a pipetting head is very space consuming and also very costly. Furthermore, a drop catcher as described before is not useful, when more than one pipetting device is mounted on a pipetting head and when these pipetting devices shall operate independently from another without increasing the potentiality of contamination of the instrument.

SUMMARY OF THE INVENTION

The present invention relates to a device for catching drops from a pipette mechanically attached to a pipetting device in the field of nucleic acid purification and amplification.

The invention further relates to a method for pipetting a liquid with a decreased potentiality of contamination of an analytical instrument as well as liquids or/and samples placed on said analytical instrument.

Moreover, the invention relates to an analytical instrument at least comprising a pipetting device, and a device for catching drops from a pipette mechanically attached to said pipetting device wherein the movement of the device for catching drops is coupled to the movement of said pipetting device.

Additionally, the invention relates to the use of a passive guidance element for mechanically coupling the movement of a device for catching drops to the movement of a pipetting device positioning said device for catching drops below the opening of said pipetting device when said pipetting device is in a parking position.

One aspect t of the invention, therefore, is to provide a device for catching drops and a method for pipetting a liquid without the application of a second actuator for moving the device for catching drops and thereby fulfilling the task of minimizing the potentiality of contamination of an analytical instrument.

According to a first aspect of the invention, this problem is solved by a device for catching drops from a pipette, said device for catching drops being mechanically attached to a pipetting device and being moveable to a position below an opening of said pipette and the movement of said device for catching drops being mechanically coupled to the movement of said pipetting device, wherein said device for catching drops comprises a frame comprising a passive guidance element for attaching said device for catching drops to said pipetting device, said pipetting device comprising a spike for linking said pipetting device and said passive guidance element, and a drop catcher container suitable for receiving and incorporating liquids when the device for catching drops is positioned below said opening of said pipette.

According to a second aspect of the invention, the above aim is attained by a method for pipetting a liquid minimizing the potentiality of contamination of an analytical instrument, liquids and/or samples placed on said analytical instrument, comprising providing on said instrument a pipetting device and a device for catching drops mechanically attached to said pipetting device, moving said pipetting device at the end of the pipetting procedure, and moving said device for catching drops to a position below the opening of said pipetting device and thereby shielding the opening of said pipetting device permitting said device for catching drops to receive and incorporate liquids emerging from said pipetting device after the end of the pipetting procedure and thereby preventing unintentional discharge of liquid onto said analytical instrument and/or liquids and samples placed onto said analytical instrument, wherein a device for catching drops according to the invention is used.

According to a third aspect of the invention, the above objective is achieved by an analytical instrument, comprising a device for catching drops according to the invention, and a pipetting device mechanically attached to said device for catching drops comprising a pipette and a spike for linking said pipetting device to the passive guidance element of said device for catching drops, wherein said device for catching drops is moveable to a position below an opening of said pipette and wherein the movement of said device for catching drops being mechanically coupled to the movement of said pipetting device.

According to a fourth aspect of the invention, the above goal is met by the use of a passive guidance element for mechanically coupling the movement of a device for catching drops to the movement of a pipetting device positioning said device for catching drops below the opening of said pipetting device when said pipetting device is in a parking position, wherein a device for catching drops according to the invention is used.

According to a fifth aspect of the invention, the above purpose is accomplished by the use of an analytical instrument comprising a pipetting device and a device for catching drops from a pipette mechanically attached to said pipetting device in the purification and/or amplification of nucleic acids, wherein said device for catching drops is passively moveable to a position below an opening of said pipette and thereby shielding the opening of said pipetting device permitting said device for catching drops to receive and incorporate liquids emerging from said pipetting device and thereby preventing unintentional discharge of liquid onto said analytical instrument and/or liquids and samples placed onto said analytical instrument, the movement of said device for catching drops is mechanically coupled to the movement of said pipetting device, and said device for catching drops is a device according to the invention.

An advantage of the invention is that due to the mechanical coupling of the movement of the device for catching drops to the movement of the pipetting device there is no necessity for the installation of a second actuator in order to move the device for catching drops to a position below the opening of said pipetting device, which is very space-and cost-saving. Furthermore, in fully automated analytical instruments this leads to reduced complexity and decreased necessity to monitor the reliability of the movement of the device for catching drops via sensors as both, the movement of the pipetting device and the movement of the device for catching drops can be monitored with only one sensor. Thus, the invention contributes to a simplified composition of the analytical instrument without the need for a second sensor for monitoring the movement of the second actuator. One sensor and one actuator are capable of controlling two different but coupled functions (movement of the pipetting device and movement of the device for catching drops).

A further advantage of the invention is that each pipetting device mounted on a pipetting head is coupled to one device for catching drops. Therefore, it is possible to operate each pipetting device independently from the other pipetting device or devices without increasing the potentiality of contamination of the instrument. The pipetting head is moved in such a way that one pipetting device is located at the desired position to perform the pipetting procedure. The movement of the pipetting device leads to the movement of the one device for catching drops positioned underneath its opening. Thereby, the opening of said pipetting device is unshielded and liquid may be dispensed from the pipetting device to the vessel. At the end of the pipetting procedure the pipetting device is moved again thereby re-shielding the opening of said pipetting device and permitting the device for catching drops to receive and incorporate liquids emerging from the pipetting device after the end of the pipetting procedure. During the pipetting procedure the openings of the other pipetting devices mounted on the pipetting head are still covered. Thus, this construction minimizes the potentiality of contamination during the pipetting procedures and the movement of the pipetting head.

BRIEF DESCRIPTION OF DRAWINGS

Certain non-limiting embodiments of the invention are described below by way of example with reference to the accompanying drawings, wherein.

DESCRIPTION OF THE PREFERRED EMBODIMENTS

Figure 1:
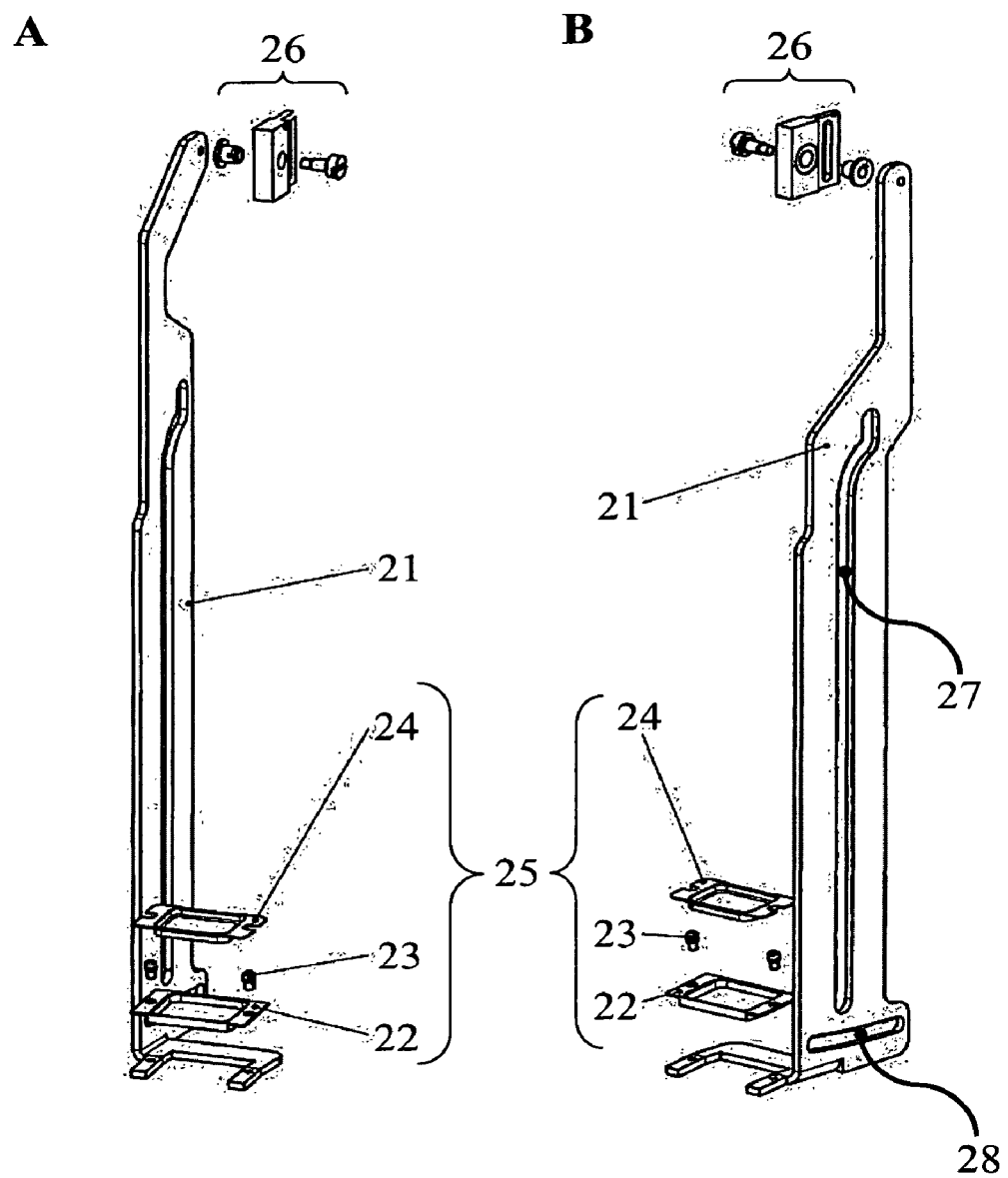
FIG. 1 shows a view of a first embodiment of the invention from a first (A) and a second (B) perspective with the tray carrier (22) fixed to the device for catching drops by fixing means (23) and the location of the removable tray (24).

As used herein, the term analytical instrument refers to an instrument capable of the automated handling and processing of samples. In certain embodiments the analytical instrument may be used for the fully automated performance of sample preparation and/or nucleic acid amplification and/or detection of amplificates.

In this connection a pipetting device comprises an integrally built pipetting module which has an inlet/outlet which may be connected to a removable pipetting tip or integrally built with a pipetting tip and can be used for aspirating or dispensing liquids. During the pipetting procedure liquid will be aspirated to or dispensed from the pipetting tip. In another embodiment the pipetting tip may be a disposable made up from one or more plastic materials (e.g. polyethylene, polypropylene). In another embodiment the pipetting tip may be a needle or a steel needle.

In certain embodiments the pipetting device is considered to be part of the analytical instrument. The pipetting device is mounted on a mounting surface in such a way that the pipetting device may be moved relative to the mounting surface. In another embodiment the pipetting device may by mounted on a pipetting head. The pipetting head may be controlled by the control unit of the analytical instrument and moved in a horizontal plane thereby providing liquid transfers from a first position in the analytical instrument to a second position in the analytical instrument.

A device for catching drops according to the invention is made up of a frame, an adjustable mounting, and a drop catcher container. In one embodiment the frame comprises at least one passive guidance element and is made up of stainless steel, aluminum, hard plastic, or composite materials. Composite materials are engineering materials made from two or more components. One component is often a strong fiber such as fiberglass, quartz, Kevlar, Dyneema or carbon fiber that gives the material its tensile strength, while another component (called a matrix) is often a resin such as polyester or epoxy that bind the fibers together, transferring load from broken fibers to unbroken ones and between fibers that are not oriented along the lines of tension. Also, unless the matrix chosen is especially flexible, it prevents the fibers form buckling in compression. In terms of stress, any fibers serve to resist tension, the matrix serves to resist shear, while all materials present serve to resist compression. The passive guidance element forms a means for mechanically coupling the device for catching drops to the pipetting device. The adjustable mounting is located at a first and upper end of the device for catching drops and functions as a means for fixing the device for catching drops to the mounting surface carrying the pipetting device. The frame comprising a passive guidance element may form a crank or a cam disk which when used in connection with the adjustable mounting may represent a mechanical drive, e.g., a cam mechanism. The main function of such a drive is the alteration of movements and of kinetic energy. In particular embodiments the vertical movement of a device may be transformed into a rotary motion by the use of such a mechanism.

The drop catcher container is positioned at the second and lower end of the device for catching drops and is suitable for receiving and incorporating liquids. Herein, the drop catcher container consist of a tray carrier, fixing means, and a removable tray. The tray carrier preferably is made up of plastics or stainless steel and may be either permanently or reversibly fixed to the frame via fixing means. Such fixing means comprise but are not limited to screws, rivets, pins, nails, spikes, glues or other adhesives and fulfill the task to permanently or reversibly attach the tray carrier to the frame. The removable tray is dimensioned and formed to easily fit into the tray carrier and may be a disposable or may be produced from an autoclavable material. In a particular embodiment the dimension of the drop catcher container is chosen such that it may incorporate the total volume of the pipetting tip, which is advantageous as even a malfunction of the pipetting device will not lead to the contamination of the analytical instrument.

In one aspect of the invention, a spike for a passive guidance element is a pin, which is dimensioned in such a way that it fits into and may slide along a passive guidance element. In a particular embodiment the pin can be spherically seated. In another embodiment the spike may comprise a head and/or a notch on the one end of the pin, which allows to allocate and fix the spike to the passive guidance element without the spike escaping the passive guidance element. A pipetting procedure in the field of the invention is considered to comprise aspiration and dispensation steps, wherein liquids may be aspirated to or dispensed from a pipetting device from or into a means for receiving liquids.

FIG. 1 shows a detailed depiction of a first embodiment of the device for catching drops from a first (A) and a second (B) perspective. The frame (21) comprises a first passive guidance element (27) and a second passive guidance element (28) for attaching the device for catching drops to the pipetting device. The device for catching drops may further comprise an adjustable mounting (26) at the upper end and a drop catcher container (25) at the lower end. The drop catcher container (25) may consist of a tray carrier (22) which is fixed to the frame (21) via fixing means (23) and a removable tray (24). In certain embodiments the frame (21) and the drop catcher container (25) roughly form a right angle. The removable tray (24) can either be a disposable or can be made up of an autoclavable material. The use of a disposable as removable tray has the advantage that the liquid in the drop catcher container can be removed and discarded with little effort. The use of an autoclavable removable tray on the other hand has the advantage that it may be reused after cleaning, reducing the amount of litter.

Figure 2:
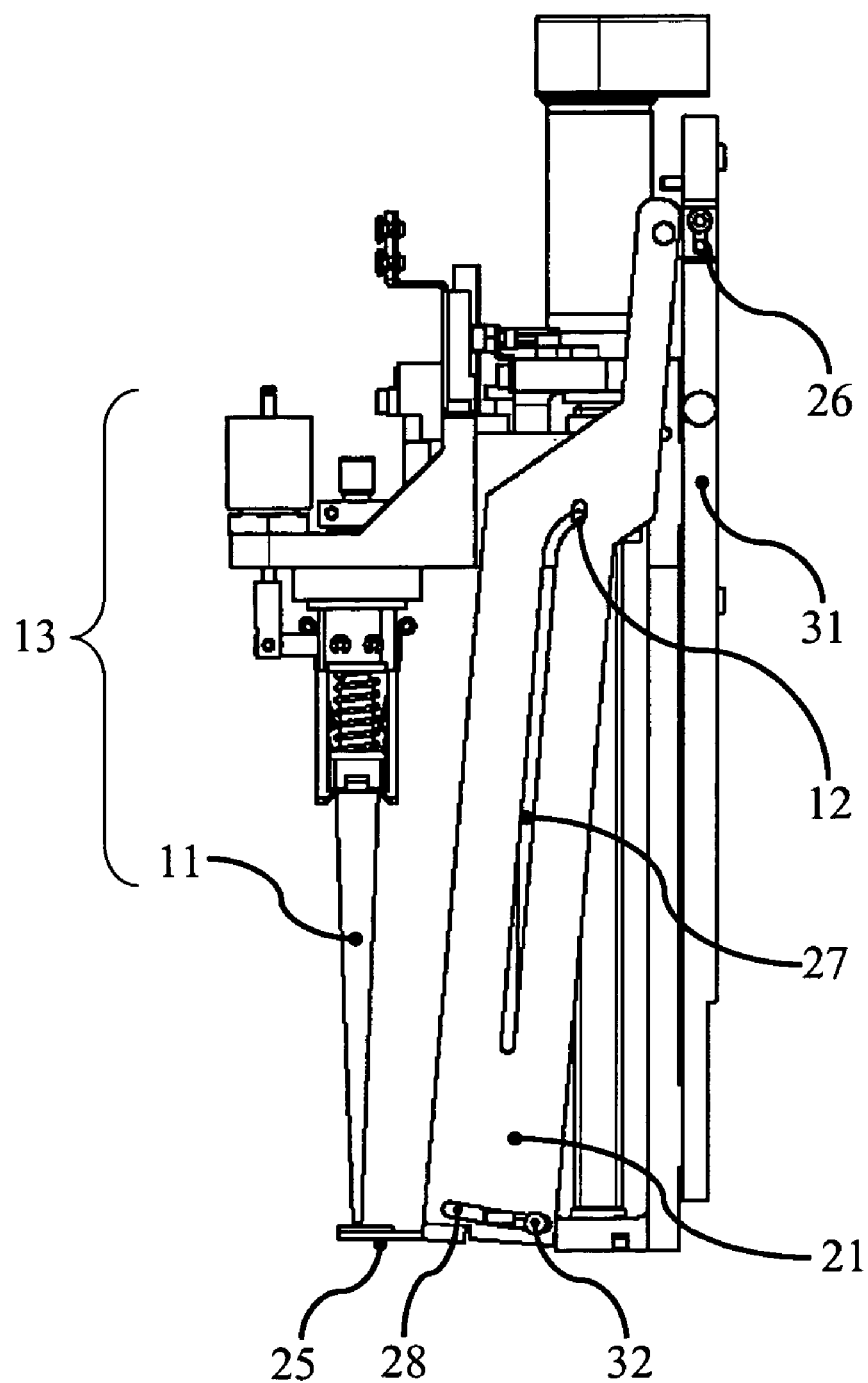
FIG. 2 shows a view of a first embodiment of the invention with the device for catching drops mechanically attached to a pipetting device (13) via spikes for a first (12) and a second (32) passive guidance element.

FIG. 2 shows the first embodiment of the device for catching drops mechanically attached to a pipetting device (13). The device for catching drops is moveable to a position below an opening of a pipetting tip (11) and this movement of the device for catching drops is mechanically coupled to the movement of the pipetting device. The coupling of both movements is firstly achieved by hooking the device for catching drops into the pipetting device by engaging the spike for the first passive guidance element (12) of the pipetting device with the first passive guidance element (27) of the device for catching drops. Secondly the upper end of the device for catching drops is connected to the mounting surface (31) carrying the pipetting device (13) via a flexible and movable adjustable mounting (26). In certain embodiments the mounting surface (31) may carry a second spike (32), which may be engaged with a second passive guidance element (28) of the frame (21). In another embodiment the second passive guidance element (28) is mostly perpendicular to the first passive guidance element (27).

Figure 3:
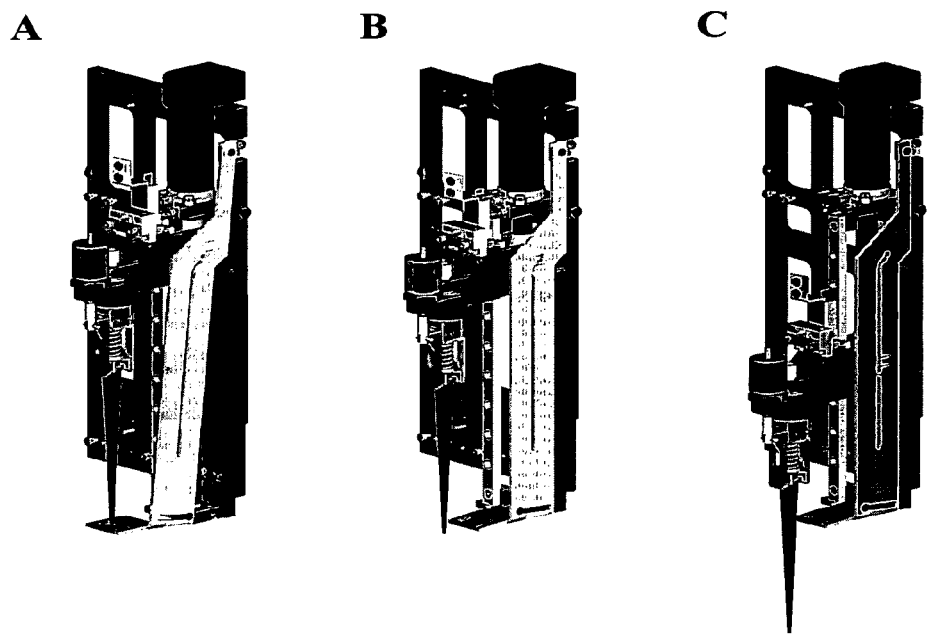
FIG. 3 shows an embodiment of the invention exemplifying a method for pipetting a liquid minimizing the potentiality of contamination of an analytical instrument with the device for catching drops mechanically attached to the pipetting device and the pipetting device in the pipetting position (A), moving at the end of the pipetting procedure (B), and the opening of the pipetting device being shielded by the device for catching drops (C).
Figure 4:
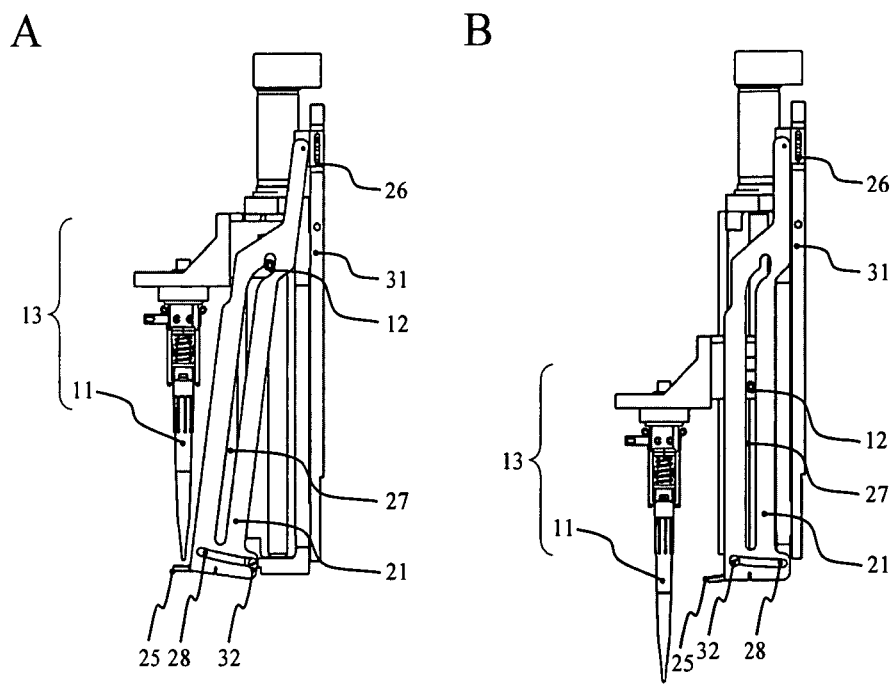
FIG. 4 shows a view of a particular embodiment of the invention with the device for catching drops mechanically attached to a pipetting device (13) via spikes for a first (12) and a second (32) passive guidance element and the opening of the pipetting device being shielded by the device for catching drops (A) as well as the pipetting device in the pipetting position (B).
Figure 5:
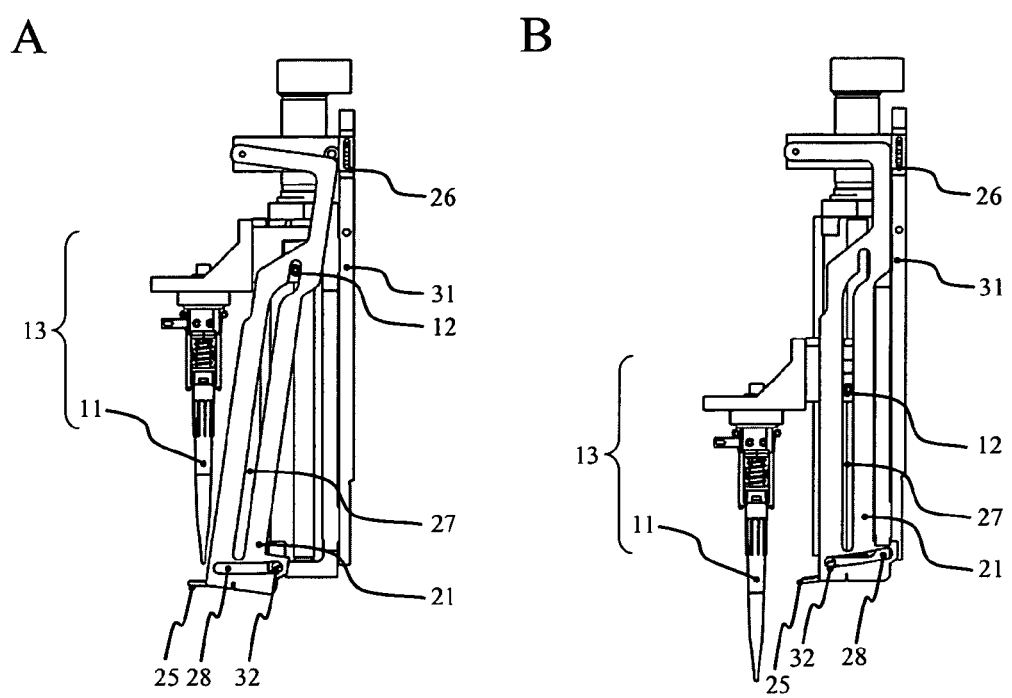
FIG. 5 shows a view of another embodiment of the invention with the device for catching drops mechanically attached to a pipetting device (13) via spikes for a first (12) and a second (32) passive guidance element and the opening of the pipetting device being shielded by the device for catching drops (A) as well as the pipetting device in the pipetting position (B).

FIG. 3 depicts different stages of the pipetting procedure using an embodiment of the device for catching drops mechanically attached to a pipetting device as outlined in above (A-C). During the pipetting procedure the pipetting device (13) is moved relative to the mounting surface (31). The starting position for a pipetting procedure is shown in FIG. 3A. The drop catcher container (25) of the device for catching drops is positioned below the opening of the pipetting tip (11) of the pipetting device (13). Due to the mechanical coupling of the pipetting device with the device for catching drops movement of the pipetting device (13) in a first direction results in the movement of the device for catching drops leading to the swing-back of the drop catcher container mediated by the interaction of the second passive guidance element (28) and the second spike (32) and thus to the exposure of the opening of the pipetting device as shown in FIG. 3B. Further movement of the pipetting device (13) allows the pipetting tip (11) to reach the position to aspirate and/or to dispense the liquid (see FIG. 3C). After the aspiration and/or dispensing of the liquid the pipetting device (13) is moved in a second direction (opposite to the first direction) in order to move the pipetting device back into the position as displayed in FIG. 3A and thereby passively again placing the drop catcher container of the device for catching drops underneath the opening of the pipetting device (13) and allowing the device for catching drops to receive and incorporate liquids emerging from the pipetting device (13). In certain embodiments the movement of the pipetting device is a vertical movement and the movement of the device for catching drops is a horizontal movement.

Figure 6:
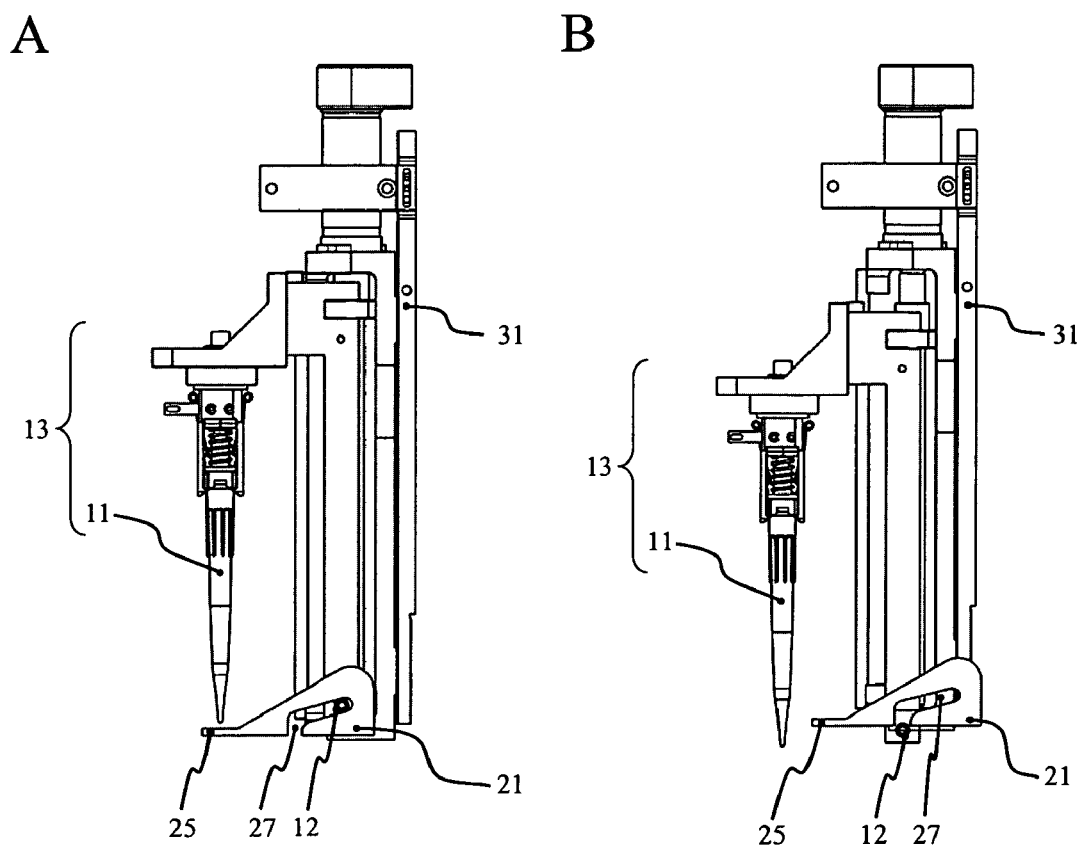
FIG. 6 shows a view of another embodiment of the invention with the device for catching drops mechanically attached to a pipetting device (13) via a spike for a first (12) passive guidance element and the opening of the pipetting device being shielded by the device for catching drops (A) as well as the pipetting device in the pipetting position (B).
Figure 7:
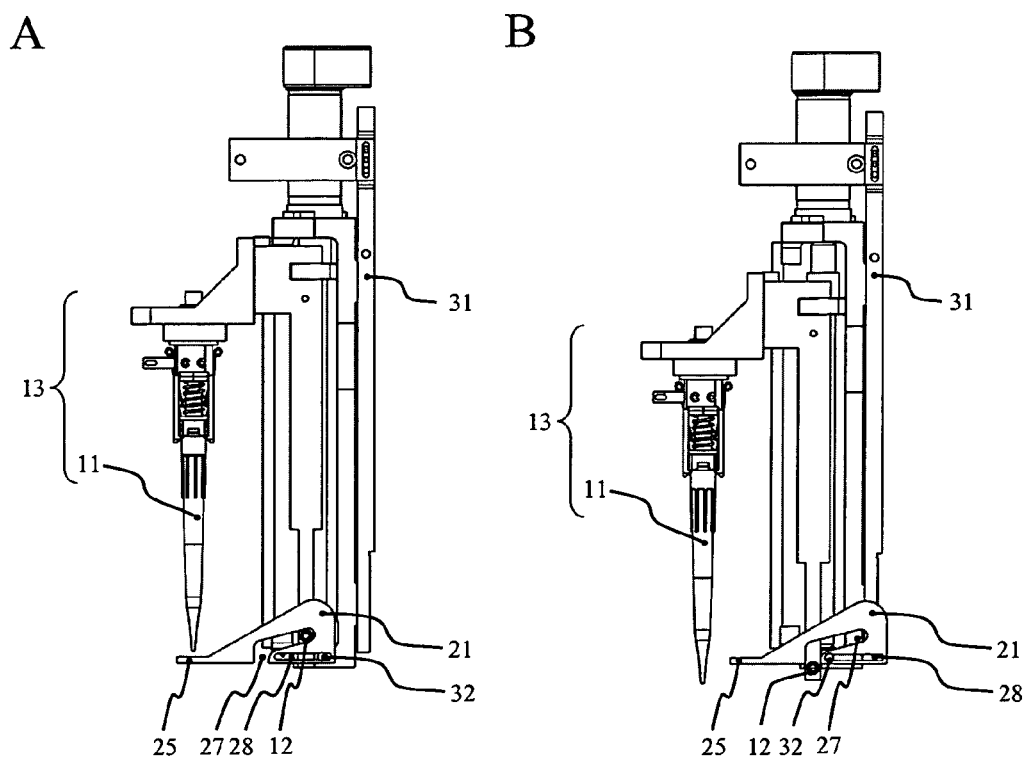
FIG. 7 shows a view of another embodiment of the invention with the device for catching drops mechanically attached to a pipetting device (13) via spikes for a first (12) and a second (32) passive guidance element and the opening of the pipetting device being shielded by the device for catching drops (A) as well as the pipetting device in the pipetting position (B).

Further embodiments of the device for catching drops mechanically attached to a pipetting device (13) via at least one spike are displayed in FIGS. 4, 5, 6, and 7. In illustration (A) of FIGS. 4, 5, 6 and 7 the opening of the pipetting device is shielded by the device for catching drops, while in illustration (B) of FIGS. 4, 5, 6 and 7 the pipetting device is in the pipetting position and the device for catching drops was moved to uncover the opening of the pipetting tip (11) caused by the mechanical coupling of the movement of the pipetting device and the pipetting device. This coupling of both movements in these embodiments may be achieved by hooking the device for catching drops into the pipetting device by engaging the spike for the first passive guidance element (12) of the pipetting device with the first passive guidance element (27) of the device for catching drops. Furthermore, the upper end of the device for catching drops is connected to the mounting surface (31) carrying the pipetting device (13) via a flexible and movable adjustable mounting (26). As displayed in the embodiments of FIGS. 4 and 5 the pivotal point of the passive guidance element (27) and the construction of the adjustable mounting (26) may vary. The mounting surface (31) of the embodiments displayed in FIGS. 4 and 5 may carry a second spike (32), which may be engaged with a second passive guidance element (28) of the frame (21). FIG. 6 shows an embodiment wherein the pipetting device comprises one spike (12) which is hooked into a passive guidance element (27) of the device for catching drops. The frame (21) of the device for catching drops is flexibly fixed to the mounting surface (31) preferably via a linear track. In this embodiment the bigger part of the passive guidance element (27) is positioned substantially perpendicular to the movement of the pipetting device (13) leading to a linear movement of the device for catching drops and thereby uncovering the opening of the opening of the pipetting tip (11). FIG. 7 depicts a particular embodiment of the device for catching drops shown in FIG. 6, wherein the mounting surface (31) additionally comprises a spike for a second passive guidance element and wherein the linear track is a second passive guidance element (32). This assembly permits a linear horizontal movement of the device for catching drops coupled to the vertical movement of the pipetting device thereby unshielding the opening of the pipetting device in order to allow for a pipetting operation of the pipetting device.

In other embodiments the pipetting device may by mounted on a pipetting head, which may be controlled by the control unit of the analytical instrument and may be moved in a horizontal plane. This embodiment has the advantage that liquid transfers from a first position in the analytical instrument to a second position in the analytical instrument may be provided without the potentiality of contaminating the analytical instrument, liquids and/or samples placed thereon.

In a further embodiment of the invention the pipetting head comprises more than one pipetting device. Particularly between 2 and 24, 2 to 16, 2 to 8, or 2 to 4 independent pipetting devices may be mounted on a pipetting head. In another embodiment each pipetting device comprises a separate device for catching drops, allowing independent pipetting procedures without increasing the potentiality of contaminating the analytical instrument and/or entities placed on the analytical instrument. Furthermore, such embodiments have the advantage that more than one pipetting procedure can be performed independently at a first location within the analytical instrument without moving the pipetting head.

Another embodiment of the invention relates to a method for pipetting a liquid minimizing the potentiality of contamination of an analytical instrument, liquids and/or samples placed on the analytical instrument. In a first step a pipetting device and a device for catching drops, which is mechanically attached to the pipetting device, is provided on the analytical instrument. At the end of the pipetting procedure the pipetting device is moved relative to the device for catching drops. As the device for catching drops is mechanically coupled to the pipetting device moving the pipetting device leads to the movement of the device for catching drops to a position below the opening of the pipetting device and thereby shielding the opening of the pipetting device permitting the device for catching drops to receive and incorporate liquids emerging from the pipetting device. Thus, unintentional discharge of liquid onto the analytical instrument and/or liquids and samples placed onto the analytical instrument is prevented.

In another embodiment the method for pipetting a liquid further comprises that a mounting surface onto which said device for catching drops is attached is provided on the analytical instrument. Initially the device for catching drops is positioned below the opening of the pipetting device. Due to the mechanical coupling of the device for catching drops to the pipetting device the movement of the pipetting device relatively and proportionately to the mounting surface before the start of the pipetting procedure results in a movement of the device for catching drops and thereby to the exposure of the opening of the pipetting device. After the exposure of the opening of the pipetting device, the pipetting procedure may be performed.

In a particular embodiment of the method for pipetting a liquid the device for catching drops is attached to the pipetting device via a passive guidance element. In certain embodiments the pipetting device is moved vertically at the end of the pipetting procedure and the device for catching drops is moved horizontally. In another embodiment the pipetting device is mounted on a pipetting head and the pipetting head may comprise between 1 and 24, between 1 and 16, between 1 and 8, or between 1 and 4 pipetting devices. The pipetting head may be controlled by a control unit of the analytical instrument and may be moved in a horizontal plane. This embodiment has the advantage that liquid transfers from a first position in the analytical instrument to a second position in the analytical instrument may be provided without the potentiality of contaminating the analytical instrument, liquids and/or samples placed thereon. In further embodiments the device for catching drops comprises a removable tray, which may either be a disposable or be made up of an autoclavable material.

Another aspect of the invention deals with an analytical instrument at least comprising a pipetting device and a device for catching drops from a pipette mechanically attached to the pipetting device, wherein the movement of said device for catching drops is mechanically coupled to the movement of said pipetting device. In a further embodiment the analytical instrument further comprises an actuator for moving the pipetting device. In another embodiment that movement of the pipetting device is a vertical movement. In a particular embodiment the analytical instrument may comprise a device for catching drops according to any embodiment described above. In another embodiment the aspiration and dispensing processes will not take place at the same position within the analytical instrument. Therefore, during this movement of the pipetting device the potentiality of contamination of the analytical instrument is reduced by means of the device for catching drops. Such an analytical instrument may be used in the fields of sample preparation and purification of biological materials (e.g. antibody-antigen testing, urine analysis), but also in nucleic acid testing (NAT), purification, amplification, and/or detection.

A further facet of the invention relates to the use of a passive guidance element for mechanically coupling the movement of a device for catching drops to the movement of a pipetting device positioning the device for catching drops below the opening of the pipetting device when the pipetting device is in a parking position. The use of such a passive guidance element has the advantage that it couples the movement of two distinct devices (e.g., a pipetting device and a device for catching drops). These two devices may be moved by one actuator, wherein the actuator actively moves a first device (e.g., the pipetting device) and the second device (e.g., the device for catching drops) is passively moved to the desired position in order to allow the second device to fulfill its designated task. Thus, for moving the second device there is no need for a second actuator and a second sensor for controlling the activity of the second actuator, which is space- and cost-saving and furthermore leads to an increased reliability. Furthermore, the passive guidance element functions as a reduction, in that the fast vertical movement of the actuation moving the pipetting device results in a smooth and relatively slow horizontal movement of the device for catching drops, when the passive guidance element mechanically couples the movement of the device for catching drops to the movement of the pipetting device. In a particular embodiment the frame (21) comprising the passive guidance element (27) may further comprise a second passive guidance element (28), which is positioned radial to an adjustable mounting (26). Thus, liquid that may be present in the removable tray (24) of the device for catching drops will not be tossed and swashed out, when the pipetting device is moved vertically.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An analytical instrument comprising:
    a pipetting device including a pipetting tip;
    an actuator for moving said pipetting device vertically, wherein said actuator moves said pipetting device between a parking position and a pipetting position;
    a device for catching drops mechanically attached to said pipetting device and being moveable to a position below the aspirating and/or dispensing opening of said pipette tip while said pipetting device is in said parking position;
    wherein said device for catching drops comprises: (i) a frame comprising a passive guidance element and (ii) a drop catcher container for movably attaching said device for catching drops to said pipetting device, said drop catcher container capable of receiving drops from said pipetting tip when the pipetting device is in said parking position and capable of exposing the opening of said pipetting device when said pipetting device is in said pipetting position;
    wherein said pipetting device comprises a spike attached to said pipetting device movably linking said pipetting device and said passive guidance element; and
    wherein the movement of said device for catching drops in and out of position below the pipetting tip is mechanically coupled to the vertical movement of said pipetting device.

2. The analytical instrument according to claim 1, wherein said drop catcher container comprises a tray carrier mounted onto said frame.

3. The analytical instrument according to claim 2, wherein said drop catcher container further comprises fixing means for fixing said tray carrier to said frame.

4. The analytical instrument according to claim 2, wherein said drop catcher container further comprises a removable tray.

5. The analytical instrument according to claim 4, wherein said removable tray is disposable.

6. The analytical instrument according to claim 4, wherein said removable tray comprises an autoclavable material.

7. The analytical instrument according to claim 1, further comprising an adjustable mounting connecting the upper end of said frame of said device for catching drops to the pipetting device.

8. The analytical instrument according to claim 1, wherein the resulting movement of said device for catching drops is a horizontal movement.

9. The analytical instrument according to claim 1, further comprising a pipetting head, wherein said pipetting head comprises between one and twenty four of said pipetting devices.

10. The analytical instrument according to claim 9, wherein each of said pipetting device comprises said device for catching drops.

11. The analytical instrument according to claim 9, wherein said pipetting head may be moved vertically and horizontally within the analytical instrument.

12. A method for pipetting a liquid minimizing the potentiality of contamination of an analytical instrument and/or samples placed on said analytical instrument, the method comprising steps of:
    providing the analytical instrument comprising the pipetting device, the actuator and the device for catching drops according to claim 1;
    moving said pipetting device to a parking position at the end of the pipetting procedure;
    moving said device for catching drops to a position below the opening of the pipetting tip while said pipetting device is in said parking position, thereby shielding the opening of said pipetting device; and permitting said device for catching drops to receive liquids dropping from said pipetting tip after the end of the pipetting procedure and thereby preventing unintentional discharge of liquid onto said analytical instrument and/or samples placed onto said analytical instrument.

13. The method according to claim 12, further comprising steps of:

moving said pipetting device to a pipetting position;

moving said device for catching drops out of the position below the opening of the pipetting tip while said pipetting device is in said pipetting position, thereby exposing the opening of said pipetting device; and performing said pipetting procedure.

* * * * *